United States Patent [19]

Funakoshi et al.

[11] 4,335,099

[45] Jun. 15, 1982

[54] EMPLOYMENT OF ENTERIC COATED IGA FOR HYPOPROTEINEMIA IN INTESTINAL INFECTIOUS DISEASES

[75] Inventors: Satoshi Funakoshi, Katano; Katuhiro Uriyu, Sakai; Yahiro Uemura; Katashi Nakane, both of Hirakata; Akio Yamane, Takatsuki, all of Japan

[73] Assignee: The Green Cross Corporation, Osaka, Japan

[21] Appl. No.: 185,929

[22] Filed: Sep. 10, 1980

Related U.S. Application Data

[63] Continuation of Ser. No. 667,193, Mar. 15, 1976, abandoned.

[30] Foreign Application Priority Data

May 29, 1975 [JP] Japan .................................. 50-64713

[51] Int. Cl.³ .......................... A61K 9/32; A61K 9/34; A61K 9/36; A61K 9/40; A61K 31/78; A61K 31/79; A61K 31/74; A61K 39/00
[52] U.S. Cl. .......................................... 424/32; 424/33; 424/34; 424/35; 424/37; 424/80; 424/81; 424/85; 424/87; 424/177
[58] Field of Search .................................... 424/32–38, 424/78, 80, 81, 85–89, 92, 177

[56] References Cited

U.S. PATENT DOCUMENTS

| | | | |
|---|---|---|---|
| 2,196,768 | 4/1940 | Hiatt | 424/35 |
| 2,369,218 | 2/1945 | Dick | 424/32 |
| 2,607,716 | 8/1952 | Link | 424/85 |
| 3,646,193 | 2/1972 | Michaelson | 424/85 |
| 3,786,123 | 1/1974 | Katzen | 424/35 X |
| 3,808,189 | 4/1974 | Breuer | 424/177 |
| 3,823,228 | 7/1974 | Ferris | 424/35 |
| 3,907,987 | 9/1975 | Wilson | 424/87 X |
| 3,992,521 | 11/1976 | Minor | 424/87 |

FOREIGN PATENT DOCUMENTS

| | | | |
|---|---|---|---|
| 528932 | 6/1954 | Belgium | 424/88 |
| 550833 | 5/1932 | Fed. Rep. of Germany | 424/88 |
| 453917 | 9/1936 | United Kingdom | 424/97 |
| 1037792 | 8/1966 | United Kingdom | 424/88 |

OTHER PUBLICATIONS

Bohl, Chem. Abs., vol. 82, 1975 Ab. No. 122703v.
Logan, Chem. Abs., vol. 82, 1975, Ab. No. 41397w.
Hanson, Chem. Abs., vol. 80, 1974, Ab. No. 119096c.
Burdon, Chem. Abs., vol. 79, 1973, Ab. No. 113784h.

Primary Examiner—Anna P. Fagelson
Attorney, Agent, or Firm—Cushman, Darby & Cushman

[57] ABSTRACT

A method of treating hypoproteinemia is disclosed in which an enteric film coated IgA-rich gamma globulin is administered orally to a person suffering therefrom until total serum content and plasma content are restored. The film coating is soluble in neutral or alkaline media by insoluble in acid media.

6 Claims, No Drawings

EMPLOYMENT OF ENTERIC COATED IGA FOR HYPOPROTEINEMIA IN INTESTINAL INFECTIOUS DISEASES

CROSS REFERENCE TO RELATED APPLICATIONS

This application is a continuation of our earlier application Ser. No. 667,193 filed Mar. 15, 1976 and now abandoned.

BACKGROUND OF THE INVENTION

This invention relates to a remedy for intestinal infectious diseases, comprising as major constituent IgA-containing γ-globulin. More particularly, it pertains to an oral remedy for intestinal infectious diseases, comprising an enteric-coated γ-globulin containing a high concentration of IgA (hereinafter referred to as IgA-rich γ-G) derived from human serum or plasma, and to a process for preparing said remedy.

Since the time when plasma fractionation began to be carried out commercially, γ-globulin has been in frequent use as an important drug along with albumin and now become indispensable as prophylactic and therapeutic purposes. However, it is administered exclusively by injection in preventing and treating measles, post-transfusion hepatitis, and various other infectious diseases.

The present inventors made an attempt to administer orally the γ-globulin which, heretofore, had been used in the limited way by injection, and, as the result, found that γ-globulin is surprisingly effective in preventing and treating intestinal infectious diseases when administered in the form of enteric preparation. This invention has been accomplished based on this finding and an object of the invention is to provide a preparation of γ-globulin which is suitable for the new uses.

After the human serum proteins had been revealed electrophoretically as albumin, γ-globulin, γ-globulin, and γ-globulin, it has been made clear that the immune antibody is present mainly in the γ-globulin and thus fractionated γ-globulin has become a useful and indispensable preparation for injection in prophylaxis and therapy. With the progress of research works, the immune antibody was found to be present also in γ-globulin fraction; the γ-globulin, which was previously considered to be the immune antibody, together with a part of β-globulin fraction was further classified into five major constituents of IgG, IgA, IgM, IgD, and IgE, each of which has its own physiological characteristics. Of these, IgA was found to be produced not only in the blood serum but also in secretory organs such as mammary gland, digestive organs, respiratory organs, etc., and is now believed to be present in the epithelial cells of mucous membrane.

The IgA found in the secretory organs is in the form of dimer consisting of two molecules of IgA, which are bridged with one molecule of secretory component (SC), is very stable against proteases and acidic condition, and is called secretory IgA (hereinafter referred to as S-IgA) as distinguished from the serum IgA (hereinafter referred to simply as IgA). Contrary to other immune globulins, IgA present in the form of S-IgA in the epithelial cells of mucous membrane attacks bacteria and viruses intruded thereinto, thus playing an important role in local immunity.

The breast milk contains S-IgA in high concentration (300 mg/dl on average in colostrum and 50 mg/dl on average in mature milk) and immunologically protects the infant who is incapable of internally producing a sufficient quantity of the immune antibody. This is clearly seen from the fact that a bottle-fed infant is inferior in resistance against infection than a breast-fed infant. The fact that the S-IgA given by lactation and passed through the stomach still retains its effectiveness as an immune antibody in the intestine shows that the S-IgA is not susceptible against proteases in the stomach and intestins and is stable under acidic conditions in the stomach. Some of the present inventors proved by an in vitro experiment that the S-IgA is far superior to the IgA in the resistance to acids and proteases [K. Uriu, Y. Uemura, S. Funakoshi, and T. Kano, the Physico-Chemical Biology, 18 (3), 214 (1974)]

The fact that the S-IgA given by the lactation retains its effectiveness in the intestinal tract of an infant shows that the S-IgA passed unchanged through the stomach and reached the intestinal tract. Because of the fact that the S-IgA secreted from the internal glands is present in the epithelial cells of mucous membrane, it might be considered that on arrival at the intestinal tract the S-IgA may be captured by the epithelial cells. However, since the antigen-antibody reaction proceeds comparatively rapidly and the lactation is carried out several times a day, it is quite understandable that the orally supplied S-IgA passes through the intestinal tract without being held by the epithelial cells, whereby the S-IgA acts effectively in attacking enteric-bacteria and entero-viruses.

It has been shown, on the other hand, that in the epithelial cells of mucous membrane there is also SC uncombined with IgA. The free SC is also present in an IgA-deficient patient. It is reported that when a large dose of blood plasma was administered to the IgA-deficient patient, IgA was found in the secretion of the patient [R. E. Petty, J. T. Cassidy, and D. B. Sullivan, Pediatrics, 51 (1), 44 (1973)]. Although it is presumed that this phenomenon is associated with the free SC present in the mucous membrane, the IgA in the blood stream is generally believed not to migrate into secretory organs or the migration, if any, is extremely low.

It is reported that in the IgA-deficient patient, the secretory organs secrete IgG and IgM to compensate the deficiency in IgA and the secreted IgG and IgM play the part of IgA [Proceedings of the Society for Experimental Biology and Medicine (Proceedings of Experimental Biology and Medicine)].

It is, of course, most desirable to feed an infant with the S-IgA which has been obtained from the secretion such as milk, saliva, etc. by way of concentrating and purifying treatments and made into a medical preparation or mixed with cow's milk (including processed milks). However, commercial production of such a medical preparation is extremely difficult in view of collecting raw materials.

DETAILED DESCRIPTION OF THE INVENTION

The present invention relating to a process for preparing an oral medicine containing IgA-rich γ-G is orginated from a novel, unprecedented idea of making not only IgA but also IgG and IgM more useful for the purpose of medical care by oral administration of the stabilized preparation containing IgA, IgG, or IgM, said idea having been conceived from the aforesaid informations, namely: IgA in the blood stream migrates with difficulty into secretory organs; natural feeding of the S-IgA in breast milk to an infant is carried out orally; and IgG and IgM are also capable of manifesting effectiveness at localities where IgA is deficient.

According to this invention, there is provided a remdy for intestinal infections diseases, comprising γ-globulin containing as major constituent IgA originated in human serum or plasma and a physiologically acceptable film material coated thereon, said film material being insoluble in acidic media but soluble in neutral or alkaline media.

The IgA-rich γ-globulin for use in the present invention is a γ-globulin preparation containing IgA in high concentration which is obtained from the starting material by purification in order to increase effectiveness of the objective medicine.

Preparation of the IgA-rich γ-G can be carried out by any conventional method. It is preferable, however, that HB antigen is removed and the purity is increased to a sufficiently high level.

Purification of IgA was first carried out by Heremans by use of zinc ion [Clinica Chimica Acta, 4, 96 (1959)]. Subsequently, improved procedures employ suitable combinations of purification steps using salting-out, DEAE-cellulose (diethylaminoethylcellulose), TEAE-cellulose (triethylaminoethyl cellulose), DEAE-Sephadex (supplied by Pharmacia Co., Sweden), and the like [Immunochemistry, 2, 263 (1963)]; Journal of Immunology, 91, 7 (1963); ibid. 107, 201 (1971); ibid., 95, 197 (1965)].

The IgA for medical use may be obtained according to the purification procedures described in the prior literatures. When human serum or plasma was used as starting material, fraction III paste was first obtained by the method of ethanol fractionation. The fraction III was then subjected to purification procedures such as ion-exchange chromatography on Sephadex, ammonium sulfate fractionation, gel filtration, the method of Audran et al. [Vox Sanguinis, 23, 165 (1972)], or salting-out method of Ishizaka et al. (Journal of immunology, 95, 197 (1965)] to obtain IgA-rich γ-globulin. Thus obtained IgA-rich γ-globulin containing IgA, and other γ-globulins is not suitable for oral administration as it is, because it is completely denatured by acid and enzyme of stomach. Consequently, it is necessary to stabilize the γ-globulin by an enteric coating which is soluble in neutral or alkaline media but insoluble in acidic media, so that the stabilized preparation may pass unchanged through the stomach and dissolve on reaching the intestine, releasing the contents.

The above-said enteric coating can be applied by any of the known methods by properly selecting the coating conditions such as those of temperature and of solvent. By proper selection of the coating conditions, the present inventors have succeeded in preparing an enteric medicine suitable for practical use, the proportion of the medicine denatured during the coating step having been kept within 10%.

The composition of the enteric film used in the present invention is methyl methacrylate-methacrylic acid copolymer, polyvinyl acetate phthalate, cellulose acetate succinate, hydroxypropylmethylcellulose phthalate, cellulose acetate phthalate, cellulose propionate, phthalate, and methylcellulose phthalate. All of these substances are soluble in organic solvent and can be applied as a solution of suitable concentration in alcohol, acetone, or the like onto the solid IgA-rich γ-G by spraying. As for the form of the present enteric medicine, capsule preparation is conveniently prepared by filling a commercial capsule, such as gelatin-base one, with IgA-rich γ-G, which has been obtained as mentioned above, dried and powdered, together with, if necessary, a customary diluent and coating the filled capsule with the above-mentioned enteric film. Enteric preparations in small particulated form such as microcapsules or minipellets may also be prepared. Enteric minipellets are prepared preferably by involving subcoating technique which consists in first applying a subcoating of water-soluble film to the solidified particles of IgA-rich γ-G and then further applying a coating of the aforesaid enteric film. The composition of the water-soluble film for subcoating is hydroxypropyl-celulose, hydroxypropylmethylcellulose, polyvinylpyrrolidone, vinylpyrrolidonevinyl acetate copolymer, methylcellulose, hydroxyethylcellulose, sodium carboxymethylcellulose, polyvinyl alcohol, acacia, and gelatin.

In carrying out the enteric coating, a solution of the film ingredient in an organic solvent is applied at a temperature of 50° C. or lower, preferably 30° C. or lower. The subcoating is carried out by applying an aqueous solution of the film ingredient at a temperature of 50° C. or lower, preferably 30° C. or lower; said aqueous solution may contain a small amount of an organic solvent.

It is optional to administrate the enteric preparation of IgA-rich γ-G either in the form of capsule or minipellet according to recipient. When orally administered, the enteric film dissolves on reaching the intestinal tract and ingredients are released to manifest to full extent its pharmacological effect in the intestinal tract.

The test result shown in examination example 1, for confirmation of pharmacological effect of the IgA-rich γ-G as an enteric preparation shows that IgA-rich γ-G is pharmacologically effective for infection experiment to mouse only when it is administered in the form of enteric preparation and the Examination Example 3 shows that the pharmacological effect of the enteric IgA-rich γ-G preparation is utilizable for the treatment of human diseases. Although the dosage for human may be one capsule as shown in Examples, the dosage is adjustable according to the symtoms and the magnitude of bacterial attack, because no side effect due to excessive administration was found in the animal experiments.

As explained in the foregoing, the enteric preparation of IgA-rich γ-G according to this invention is significance as an unprecedented medical use of γ-globulin. The present invention which enables the γ-globulin to manifest its pharmacological effect in the intestinal tract is certainly of great significance from the practical viewpoint.

EXAMPLE 1

Three hundred liters of water was added to 31 kg of the fraction III paste obtained by the Cohn's ethanol fractionation method from 1,000 liters of pooled blood plasma of normal adults. The resulting mixture was thoroughly mixed to form a uniform suspension and then centrifuged to collect the supernatant. To the supernatant was added 45 kg of QAE-Sephadex A-50 which had been equilibrated with a 0.0063 M solution of EDTA-4Na. The mixture was thoroughly mixed and filtered to collect the Sephadex loaded with adsorbed phase. The loaded Sephadex was thoroughly mixed with 150 liters of 0.26 M acetate buffer solution (pH 4.0)

and filtered to collect the eluate. The eluate was concentrated by the ammonium sulfate precipitation method and freeze-dried in vacuo to obtain 187 g of IgA-rich γ-G in powder form of the following composition: 52% IgA, 44%, IgG, 1.5% IgM, and 2.5% others. The HB antigen was found negative by radioimmunoassay method. A dose of 300 mg was orally administered to mice, each 20±2 g in body weight. The follow-up was made for one week without noting any abnormality.

To 100 g of the IgA-rich γ-G obtained above, was added 200 g of a base mixture comprising 55% of cornstarch, 43.8% of Avicel, and 1.2% of magnesium stearate. Each 120±10 mg of the thoroughly blended mixture was filled in No. 3 gelatin capsules. The filled capsules were applied by spraying with a filming solution comprising 8% of cellulose acetate phthalate, 56% methyl ethyl ketone, 35% of methylene chloride, and 1% of triacetine to obtain enteric capsules containing IgA-rich γ-G. Yields of main constituents (IgA and IgG) in final products were as shown in Table 1.

TABLE 1.

| Yield of the main constituent in IgA-rich γ-G enteric capsules. | | IgA | IgG |
|---|---|---|---|
| Average amount filled in a capsule | | 20.8 mg | 17.6 mg |
| Yield (single radial immunodiffusion method) | | 17.9 mg | 15.7 mg |
| Recovery (%) | | 86% (a) | 89% (b) |
| Measles antibody potency | Potency unit/100 mg IgA-rich γ-G | | 7.6 |
| | Potency in unit per calculated of IgA-rich γ-G encapsulated Yield (c) | | 7.3 |
| Yield of potency | | 112% | 96% |
| Yield of antigenicity $\left(\frac{c}{a} \text{ and } \frac{c}{b}\right)$ | | | 102% |

EXAMPLE 2

In 30 liters of cold water, was suspended 3 kg of the Cohn's fraction III paste. The suspension was left standing overnight to separate the supernatant. According to the procedure of L.P.R. Audran and M. Steinbuch [Vox Sanguinis, 23, 165 (1972)], 900 g of sodium caprylate was added to the above supernatant to adjust pH to 5.0. The precipitates were removed by filtration and the filtrate was diluted with cold ethanol to a final concentration of 33% to precipitate IgA-rich γ-G. The precipitates were separated, dissolved in a 2-% glycine solution containing 1% of sodium chloride, and centrifuged to remove insolubles. The clear solution was fractionated on a column of Sephadex G-200 (Pharmacia Co., Sweden), which had been equilibrated with the same glycine solution as used above. The fraction containing IgA-rich γ-G was freeze-dried to yield 28 g (in terms of protein) of a powder of the following composition: 62% of IgA, 27% of IgG, 3% of IgM, and 8% of other proteins. Thus obtained IgA-rich γ-G sample was found negative in HB antigen activity, as tested by radioimmunoassay method. Each 300 mg (in terms of protein) of the sample was orally administered to mice, each 20±2 g in body weight, and the follow-up was made for one week without noting any abnormality.

To 25 g of the IgA-rich γ-G obtained above, was added 25 g of an excipient mixture comprising 60% of cornstarch, 39% crystalline cellulose, and 1% of magnesium stearate. Each 50±5 mg of the thoroughly blended mixture was filled in No. 5 capsules. The filled capsules were applied with a filming solution comprising 10% of a methyl methacrylate-methacrylic acid copolymer, 50% of acetone, 38% of isopropanol, and 2% of triacetin to obtain enteric capsules containing IgA-rich γ-G. Yields of main constituents (IgA and IgG) in final products were as shown in Table 2.

TABLE 2.

| Yield of the main constituent in IgA-rich γ-G enteric capsules | | IgA | IgG |
|---|---|---|---|
| Average amount filled in a capsule | | 15.5 mg | 6.75 mg |
| Yield (single radial immunodiffusion method) | | 14.3 mg | 6.08 mg |
| Recovery (%) | | 92% (a) | 90% (b) |
| Measles antibody potency | Potency in unit/100 mg IgA-rich γ-G | | 7.0 |
| | Potency in unit amount of 100 mg of IgA-rich γ-G encapsulated Yield (c) | | 7.0 |
| Yield of potency | | 109% | 100 |
| Yield of antigenicity $\left(\frac{c}{a} \text{ and } \frac{c}{b}\right)$ | | | 111% |

No abnormality was noted in the safety test to mice.

EXAMPLE 3

To 1,000 liters of pooled blood plasma of normal adults, was added 10,000 liters of cold water and pH was adjusted to 5.3. The precipitates formed were removed by centrifugation. In order to purify IgA-rich γ-G, the supernatant obtained by centrifugation was subjected to the salting-out procedure according to K. Ishizaka, T. Ishizaka, E. H. Lee, and H. Fudenberg [Journal of Immunology, 95, 197 (1965)] in the following way.

Zinc sulfate was added to the supernatant until a concentration of 0.05 M is reached. The precipitates formed again were removed by centrifugation. Ammonium sulfate was added to the supernatant to a concentration of 45% saturation to fractionate IgA as precipitates. The precipitates were collected by centrifugation, then dialyzed against 2-% glycine solution or isotonic saline, and freeze-dried to obtain 184 g of IgA-rich γ-G in powder form of the following composition: 67% of IgA, 22% of IgG, 8% of albumin, and 3% of other proteins; the HB antigen activity was found negative, as tested by radioimmunoassay method. Each 300 mg of the sample was orally administered to mice, each 20±2 g in body weight, and the follow-up was made for one week without noting any abnormality.

To 150 g of the IgA-rich γ-G obtained above, was added 600 g of a base mixture comprising 70% of cornstarch, 20% of Avicel, 5% of calcium carboxymethylcellulose 505, and 5% of hydroxypropylcellulose (HPC). The resulting mixture was moistened, granulated to spherical granules, and dried in vacuo to obtain 750 g of granules, about 0.5 mm in diameter. The granules were applied with a subcoating solution prepared by dissolving a powdered mixture of 80% of polyvinylpyrrolidone (PVP) and 20% of HPC in water. Thereafter, a filming solution comprising 10% of cellulose propionate phthalate, 49% of acetone, 40% of isopropanol, and 2% of triacetin was applied to the subcoated granules to obtain enteric minipellets. The increase in total weight of the minipellets after film coating was 40%. The survival of IgA and IgG in the final product and the antibody activity were as shown in Table 3.

TABLE 3.

| Yield of the main constituent in IgA-rich γ-G enteric minipellets | | | |
|---|---|---|---|
| | | IgA | IgG |
| Average amount filled in 1 g of minipellets | | 58 mg | 49 mg |
| Yield (single radial immunodiffusion method) | | 48 mg | 42 mg |
| Recovery (%) | | 82% (a) | 85% (b) |
| Measles antibody potency | Potency in unit/ 100 mg of IgA-rich γ-G | | 7.6 |
| | Potency in unit per calculated amount of 100 mg of IgA-rich γ-G filled in minipellets | | 7.0 |
| | Yield (c) | | 92% |
| Yield of potency Yield of antigenicity $\left(\frac{c}{a} \text{ and } \frac{c}{b}\right)$ | | 112% | 108% |

EXAMINATION EXAMPLE 1

The infection test for confirming pharmacological effect of the enteric IgA-rich γ-G preparation was carried out on the prevention of typhoid bacillus infection. The sample (A) for the test was 23 mg (3 mg in terms of protein) of the enteric IgA-rich γ-G minipellets obtained in Example 3 and the control sample (B) was 15 mg (3 mg in terms of protein) of IgA-rich γ-G without enteric coating, obtained in Example 3. For comparison, there was used 23 mg (3 mg in terms of protein) of the enteric IgA-rich γ-G minipellets (C) prepared in a manner similar to that in Example 3 from human blood plasma immunized with typhoid and paratyphoid vaccin. Six hours before bacillus challenge, the samples were orally administered respectively to four-membered groups of 4-weeks-old mice. Strain 63 typhoid bacillus suspended in a 3-% mucin solution was used for the challenge in varied concentrations from $10^{-1}$ to $10^{-9}$ mg/ml. Each mouse was inoculated with 0.1 ml of the bacillus suspension into the small intestine and the mortality was inspected for 3 days. The results obtained were as shown in Table 4. It was found that as is apparent from Table 4, only the enteric preparation had infection-preventing effect.

EXAMINATION EXAMPLE 2

The safety test for the enteric IgA-rich γ-G capsule obtained in Example 1 was carried out by orally administering the capsule to mice, each 20±2 g in body weight, for three consecutive days and observing the progress for one week. No abnormality was noted.

EXAMINATION EXAMPLE 3

An example of clinical application of the enteric IgA-rich γ-G preparation is described below.

The patient was a 12-years-old boy, diagnosed to be agammaglobulinemia and suffering from watery diarrhea, anemia, and pleurisy.

Immediately after hospitalization, antibiotics and immune serum globulin were administered intramuscularly or intravenously. As the result, the symtoms of pleurisy were improved but fever and diarrhea were not improved and the lack of appetite continued. Hypoproteinemia symtoms became serious, total protein content and albumin content of the serum having been decreased to 4.0 g/dl and 1 g/dl, respectively.

On the 26th day of hospitalization, oral administration of the enteric IgA-rich γ-G preparation obtained in Example 1 was started. The capsule was administered 3 times a day (each time one capsule containing 50 mg of IgA) between meals. Three days after commencement of administration, the fever began to decrease and became normal on the seventh day of administration. Excrement became normal on the fourth day. Since then, neither pyrexia nor diarrhea recurred; appetite was gradually improved; symptoms of hypoproteinemia were improved, total protein content and albumin content of serum having been increased to 6.4 g/dl and 4.2 g/dl, respectively; and marked improvement in general symptons of the patient was confirmed. After 95 days of hospitalization, the patient was released.

What is claimed is:

1. A method of treating hypoproteinemia caused by diarrhea and anorexia due to bacillary intestinal infectious diseases, said method comprising orally administering an effective amount therefor of an enteric film-coated IgA rich gamma globulin originated in human serum or plasma to a person suffering from hypoproteinemia.

2. The method as claimed in claim 1 wherein said pharmaceutical dosage contains about 50 mg of IgA.

3. The method as claimed in claim 2 wherein said dosage is administered 3 times a day.

4. The method as claimed in claim 1 wherein said pharmaceutical dosage has a subcoating of a water-soluble film and a top enteric coating of an organic solvent soluble film.

5. The method as claimed in claim 1 or 4 wherein said film is a film soluble in organic solvents selected from

TABLE 4

| Magnitude of challenge bacillius (mg/0.1 ml) | | $10^{-1}$ | $10^{-2}$ | $10^{-3}$ | $10^{-4}$ | $10^{-5}$ | $10^{-6}$ | $10^{-7}$ | $10^{-8}$ | $10^{-9}$ |
|---|---|---|---|---|---|---|---|---|---|---|
| Sample | A | 4/4 | 4/4 | 3/4 | 2/4 | 1/4 | 0/4 | 0/4 | 0/4 | 0/4 |
| | B | 4/4 | 4/4 | 4/4 | 4/4 | 4/4 | 4/4 | 4/4 | 2/4 | 0/4 |
| | C | 4/4 | 3/4 | 2/4 | 1/4 | 0/4 | 0/4 | 0/4 | 0/4 | 0/4 |
| No treatment | | 4/4 | 4/4 | 4/4 | 4/4 | 4/4 | 4/4 | 4/4 | 4/4 | 4/4 |

Note:
(1) Sample form: oral minipellets.
(2) Samples were orally administered.
(3) Denominator of the fractional figure represents number of test animals and numerator represents number of dead animals.

the group consisting of methyl methacrylate-methacrylic acid copolymer, polyvinyl acetate phthalate, cellulose acetate succinate, hydroxypropylmethylcellulose phthalate, cellulose acetate phthalate, cellulose propionate phthalate, and methylcellulose phthalate.

6. The method as claimed in claim 4 wherein said water soluble film is selected from the group consisting of hydroxypropylcellulose, hydroxypropylmethylcellulose, polyvinylpyrrolidone, vinylpyrrolidone-vinyl acetate copolymer, methylcellulose, hydroxyethylcellulose, sodium carboxymethylcellulose, polyvinyl alcohol, acacia, and gelatin.

* * * * *